United States Patent [19]

Portney et al.

[11] Patent Number: 5,196,028
[45] Date of Patent: Mar. 23, 1993

[54] HIGH-MAGNIFICATION TELEPHOTO SPECTACLES FOR AGE-RELATED MACULAR DEGENERATION

[75] Inventors: Valdemar Portney, Irvine, Calif.; Jeffrey E. Koziol, Arlington Hgts., Ill.

[73] Assignee: Allergan, Inc., Irvine, Calif.

[21] Appl. No.: 730,471

[22] Filed: Jul. 16, 1991

Related U.S. Application Data

[60] Continuation-in-part of Ser. No. 690,814, Apr. 23, 1991, Pat. No. 5,088,809, which is a division of Ser. No. 141,482, Jan. 5, 1988, Pat. No. 5,030,231.

[51] Int. Cl.$^5$ .......................... A61F 2/16; G02C 1/00
[52] U.S. Cl. .......................... 623/6; 351/41; 351/158
[58] Field of Search .............. 623/6; 350/145, 204; 351/41, 158, 167

[56] References Cited

U.S. PATENT DOCUMENTS

| | | | |
|---|---|---|---|
| 2,024,322 | 12/1935 | Wittig | 351/158 X |
| 2,389,428 | 11/1945 | Glasser | 351/158 |
| 3,273,456 | 9/1966 | Feinbloom | 351/158 X |
| 4,074,368 | 2/1978 | Levy, Jr. et al. | 623/6 |
| 4,155,626 | 5/1979 | Grech | 351/41 X |
| 4,540,238 | 9/1985 | Edwards . | |
| 4,637,696 | 1/1987 | Wilkins | 351/41 |
| 4,666,446 | 5/1987 | Koziol et al. | 623/6 |
| 4,710,197 | 12/1987 | Donn et al. | 623/6 |
| 4,863,468 | 9/1989 | Feinbloom et al. | 623/6 |
| 4,957,506 | 9/1990 | Mercier | 623/6 |

FOREIGN PATENT DOCUMENTS

| | | |
|---|---|---|
| 63-321 | 6/1986 | Japan . |
| WO87/04264 | 7/1987 | PCT Int'l Appl. . |
| 400610 | 4/1966 | Switzerland . |

OTHER PUBLICATIONS

"Use of Low-Magnification Telescopes As Optometers in Low Vision", George Woo, O.D., Ph.D., *Optometric Monthly*, pp. 174-151, May 1978.

*Primary Examiner*—Ronald Frinks
*Attorney, Agent, or Firm*—Gordon L. Peterson

[57] ABSTRACT

A ophthalmic lens system comprising an intraocular lens adapted for implantation in the eye and spectacles. The intraocular lens has a negative IOL portion. The spectacles include a positive lens system for directing light toward the negative lens portion of the intraocular lens. The positive lens system includes a positive lens and a negative lens, with the negative lens being located posteriorly of the positive lens.

10 Claims, 2 Drawing Sheets

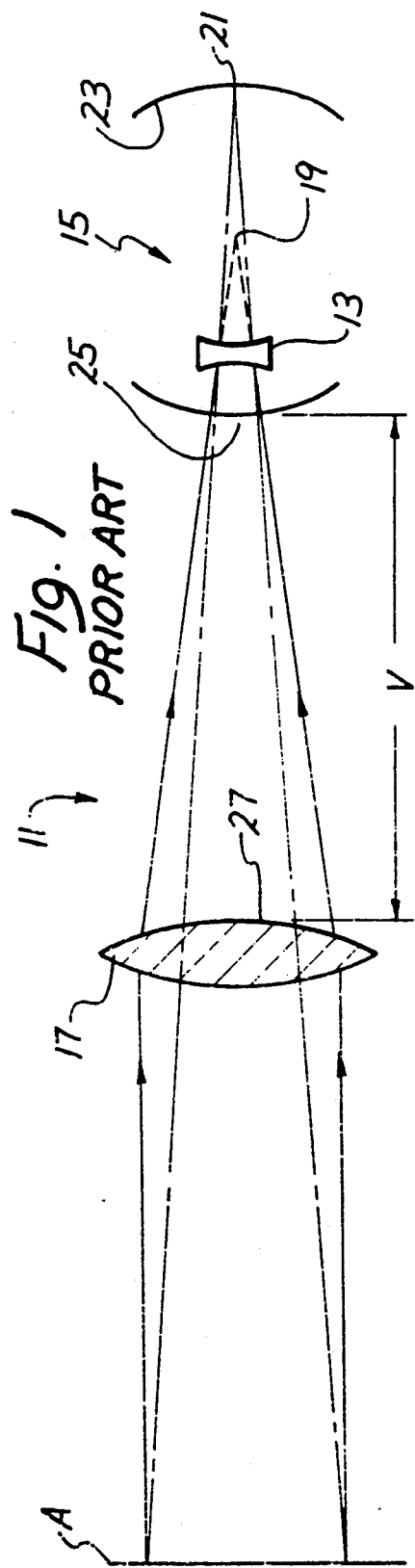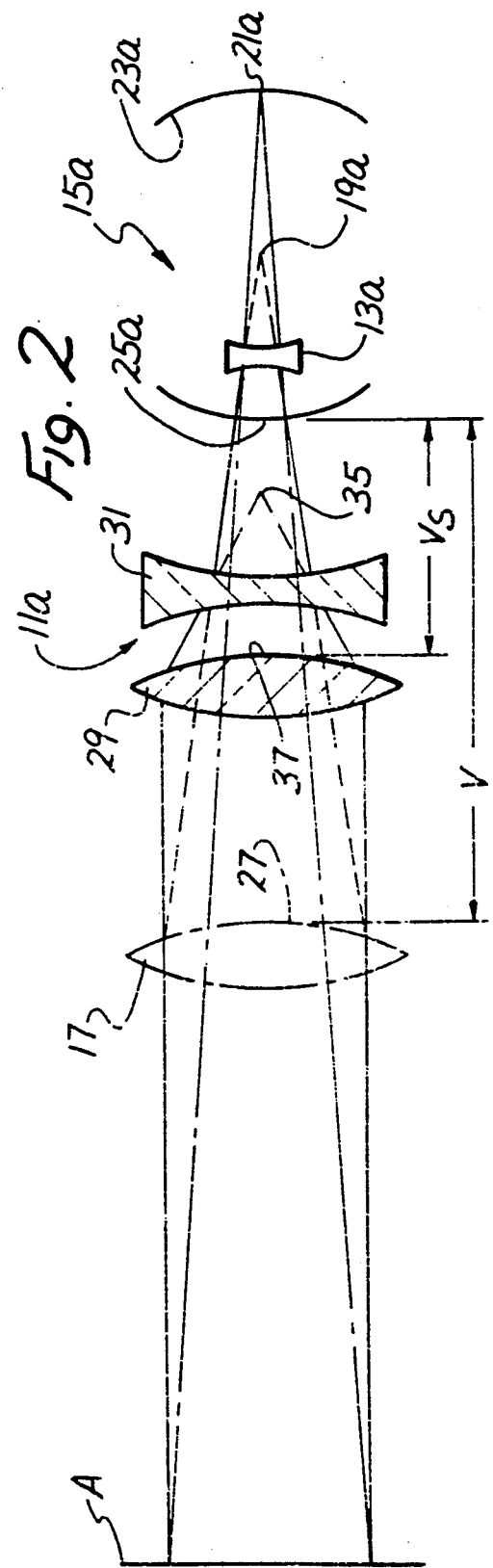

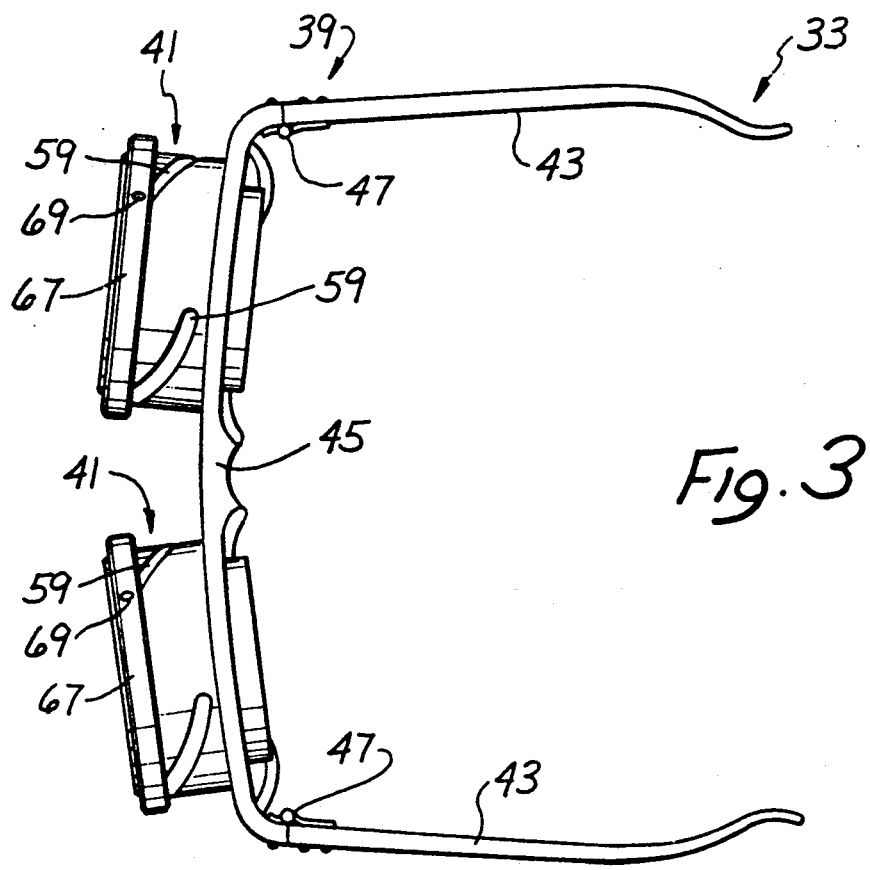
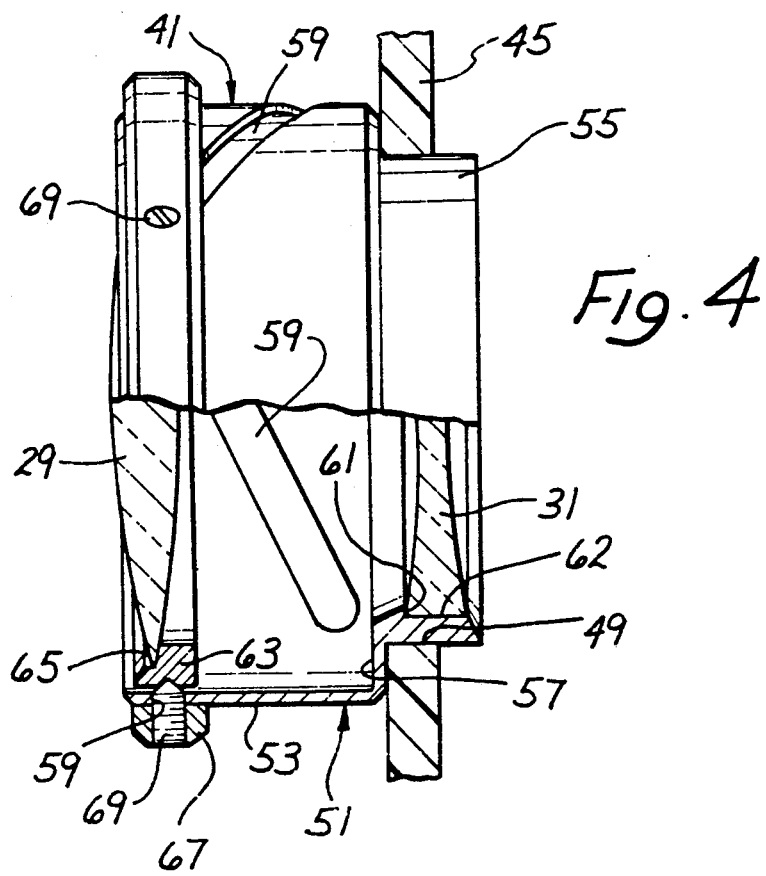

HIGH-MAGNIFICATION TELEPHOTO SPECTACLES FOR AGE-RELATED MACULAR DEGENERATION

This application is a continuation in part of Ser. No. 690,814 filed Apr. 23, 1991, now U.S. Pat. No. 5,088,809, which is a division of Ser. No. 141,482 filed Jan. 5, 1988, now U.S. Pat. No. 5,030,231.

FIELD OF THE INVENTION

This invention relates generally to an ophthalmic lens system and more particularly to a system which includes, in combination, telephoto spectacles and an intraocular lens having a negative lens portion.

BACKGROUND OF THE INVENTION

Macular degeneration, which is generally age-related, affects a central region of the retina known as the macula. Macular degeneration can lead to a gradual or rapid loss of vision to the level of 20/200 or less. It may affect, for example, only about ¼ to 4 square millimeters of the macula, thereby leaving 95 to 99 percent of the retina unaffected. Accordingly, central vision, such as for reading and watching television, can be lost while peripheral vision remains relatively intact.

Vision problems for the patient are compounded if macular degeneration is also accompanied by cataracts on the natural lens of the affected individual. One way of dealing with this compounded vision problem is disclosed in Donn et al U.S. Pat. No. 4,710,197. The disclosed approach is to replace the cataractic natural lens of the eye with a negative intraocular lens and to employ a single, positive lens element on a spectacle frame in combination with the intraocular lens (IOL). A positive or negative contact lens may also be used in this system to further correct the patient's vision.

Another approach is disclosed in grandparent Portney application Ser. No. 141,482 filed on Jan. 5, 1988, and entitled Teledioptric Lens System. This application is incorporated by reference herein. This latter approach is disclosed as employing an IOL with a negative IOL portion and bi-element spectacles serving as a positive lens to direct light toward the negative lens portion of the IOL. The bi-element spectacles are not telephoto, but when used with the negative IOL portion, a single telephoto lens system is provided.

Both of these approaches improve the compound vision problem referred to above. However, the contact lens-single spectacle lens combination disclosed in the Donn et al patent suffers from problems of maintaining alignment between the contact lens and the spectacle lens and other problems commonly associated with wearing of contact lenses. Also, for larger system magnification, e.g., greater than 3× for far vision and greater than 4.5× for near vision, the system of Ser. No. 141,482 requires a relatively large vertex distance, i.e., the spacing between the outer surface of the eye and the spectacle lens. This reduces the field of fixation, i.e., the maximum angle within which the eye can move and still see an object clearly and tends to make the spectacles less comfortable to wear and not aesthetically pleasing. The large vertex distance also tends to draw attention to the visual handicap of the wearer.

SUMMARY OF THE INVENTION

The present invention provides an ophthalmic lens system which generally overcomes the problems discussed above. The ophthalmic lens system of this invention includes an IOL and multiple element spectacles. For a given relatively high magnification, the vertex distance is substantially reduced as compared with the vertex distance necessary to accomplish that same magnification in the system of Ser. No. 141,482.

This invention can be embodied in an ophthalmic lens system which includes an IOL adapted for implantation in the eye and having a negative IOL portion and multiple-element spectacles which provide a positive lens system for directing light toward the negative lens portion. The positive lens system includes a positive lens and a negative lens, with the negative lens being located posteriorly of the positive lens.

By using a positive lens and a negative lens as part of spectacles rather than single or multiple positive lenses, the vertex distance can be reduced. Accordingly, high magnification with a wide field of fixation can be obtained at relatively short vertex distances.

The positive and negative lens may be the only refracting elements of the positive lens system of the spectacles or additional refracting elements may be provided, if desired. Because all of the external lenses of the positive lens system form a part of spectacles, the problem of alignment between a contact lens and a spectacle lens is avoided, and the other problems of wearing contact lenses are also eliminated.

Viewed from a different perspective, the spectacles include a telephoto lens system with the telephoto lens system including a plurality of lenses each having a power other than unity. The telephoto lens system refracts light similar to a single-element spectacle lens placed at a long vertex distance. By using the telephoto lens system, the usual advantages of spectacles can be obtained, and the vertex distance can be reduced.

A telephoto lens system is a lens system in which the focal length of the lens system is longer than the overall dimension of the lens system. With this invention, the IOL cooperates with the telephoto lens system of the spectacles to provide a second telephoto lens system. This double-telephoto lens system can be used to provide substantial magnification without requiring an excessive vertex distance.

Not only does the use of multiple element spectacles as described above provide for a relatively short vertex distance and a wider field of fixation at relatively high magnifications, but multiple-element spectacles have other advantages. For example, the lenses of multi-element spectacles can be made thinner and therefore possibly lighter than a single larger lens.

The positive and negative lens elements are preferably carried by a spectacle frame in axially spaced relationship. In a preferred construction, the axial spacing between the positive and negative lens elements can be adjusted without varying the vertex distance by which the negative lens is spaced from the eye. This axial adjustment enables the user to adjust the power of the telephoto lens system without adjusting the vertex distance between the negative or posterior lens and the eye.

Any correction for astigmatism is characteristically placed on the most posterior lens surface. By allowing the posterior lens to remain stationary, this astigmatism correction is not upset as it might be if the posterior lens were allowed to move axially.

The invention, together with additional features and advantages thereof, may best be understood by refer-

3 ence to the following description taken in connection with the accompanying illustrative drawings.

BRIEF DESCRIPTION OF THE DRAWINGS

FIG. 1 is a schematic illustration of a prior art ophthalmic lens system.

FIG. 2 is a schematic illustration of an ophthalmic lens system constructed in accordance with the teachings of this invention and illustrating how the ophthalmic lens system of this invention reduces the vertex distance.

FIG. 3 is a plan view of one form of multiple-element spectacles that can be used with this invention.

FIG. 4 is an elevational view partially in section of one mounting section and an adjacent portion of the spectacle showing the mounting of the positive and negative lens sections.

DESCRIPTION OF THE PREFERRED EMBODIMENT

FIG. 1 shows a prior art ophthalmic lens system 11 which includes a negative IOL 13 implanted in a human eye 15 and a positive external lens 17 adapted to be carried by a spectacle frame (not shown). Corneal power is ignored in FIG. 1. The lens 17 represents one or more positive lenses. Parallel light passing through the lens 17 is directed by the lens toward a focal point 19 of the external lens 17. The IOL 13 is between the external lens 17 and its focal point 19, and it redirects the light received from the external lens 17 toward a focal point 21 on the retina 23.

The system 11 functions as a Galilean telescope having a magnification greater than unity. The magnification that is achieved with the lens system 11 is a function of, among other things, a vertex distance V between an outer surface 25 of the eye and a posterior surface 27 of the exterior lens 17.

FIG. 2 shows a lens system 11a constructed in accordance with the present invention in which corneal power is also ignored. Portions of FIG. 2 corresponding to portions of FIG. 1 are designated by corresponding reference numerals followed by the letter "a".

The system 11a includes a positive lens 29 and a negative lens 31 arranged with the negative lens posterior to the positive lens so that it is located between the positive lens and the eye 15a. In this embodiment, the positive lens 29 is biconvex, and the negative lens 31 is biconcave; however, this is merely illustrative. The lenses 29 and 31 are sized and adapted to be mounted on a spectacle frame 33 (FIG. 3). Although the lenses 29 and 31 are the only refracting external lens elements of the system 11a, this also is merely illustrative in that either or both of the lenses 29 and 31 may comprise multiple lenses, if desired.

The positive lens 29 directs incoming parallel light toward a focal point 35 of the positive lens, and the negative lens 31 redirects this light toward the negative IOL 13a and to a focal point 19a of the negative lens 31. The negative IOL 13 functions as described above to form an image at a focal point 21a on the retina 23a.

The lens 17 of FIG. 1 is shown in FIG. 2 in phantom lines. The lens 17 is spaced from the eye 15a a sufficient distance so that its focal point is at the focal point 19a. When so positioned, the lens 17 is spaced by a vertex distance V from the eye 15a. Specifically, the vertex distance V is the distance between the posterior surface 27 of the lens 17 and the outer surface 25a of the eye 15a.

4

So far as magnification is concerned, the lens 17 in combination with the IOL 13a would provide the same magnification as the lenses 29 and 31 in combination with the IOL 13a. However, the lens 29 is separated by a relatively short vortex distance $V_s$ from the eye 15a. Specifically, the vertex distance $V_s$ is the distance between a posterior surface 37 of the positive lens 29 and the outer surface 25a of the eye 15a. As shown in FIG. 2, the vertex distance $V_s$ is much less than the vertex distance V. Consequently, the lens system 11a of this invention can provide the same magnification as the prior art system of FIG. 1 but at a much reduced vertex distance and with a consequently greater field of fixation. For example, the lens system 11a can provide a magnification of $4.5\times$ for near or $3\times$ for far with a vertex distance $V_s$ of no more than 20 mm.

It is also apparent from FIG. 2 that the lens system 11a includes two telephoto lens systems. The first telephoto lens system comprises the lenses 29 and 31. This lens system is telephoto because its focal length, which extends from the lens 17 to the focal point 19a is greater than the system length which extends from the lens 29 to the focal point 19a. The system 11 of FIG. 1 does not have this telephoto system.

In addition, the lenses 29 and 31 cooperate with the IOL 13a to form a second telephoto lens system. The focal length of this system is from a plane A to the focal point 21a, and this is greater than the length of the system which extends from the lens 17 to the focal point 21a. The plane A in FIGS. 1 and 2 is the location of the lens 17 if it alone were to provide an image on the retina at the same power as the lenses 29, 31 and 13a. The prior art system of FIG. 1 also has this latter telephoto system.

The lenses 29 and 31 may be suitably mounted on a spectacle frame in any desired manner, and the spectacle frame 33 and the manner of mounting the lenses on this frame shown in FIGS. 3 and 4 is purely illustrative. When mounted on the frame 33, the resulting spectacles include a telephoto lens system, i.e., the lenses 29 and 31. FIG. 3 shows spectacles 39 which comprise the frame 33, two sets of the lenses 29 and 31 and two mounting sections 41 for mounting the sets of the lenses 29 and 31, respectively, on the spectacle frame 33. The lenses 29 and 31 of each set are in axial alignment so they may be worn in alignment with the optical axis of the eye. The spectacle frame 33 comprises a pair of temples 43, a front section 45 and couplings 47 for pivotally attaching the temples to the opposite ends of the front section in a conventional manner. The front section 45 has a pair of openings 49 (only one being shown in FIG. 4) for receiving portions of the mounting sections 41, respectively. Thus, the frame 33 may be essentially of conventional construction, except that it is adapted to receive and mount the mounting sections 41 rather than conventional eyeglass lenses. The frame 33 may be constructed of any of the usual eyeglass frame materials, including metals and polymeric materials.

In this embodiment, each of the mounting sections 41 may be identical, and only one of them is shown and described in detail herein. The mounting section 41 includes a tubular housing 51 open at both ends and including a large-diameter portion 53 and a small-diameter portion 55 integrally joined by a shoulder 57. The small-diameter portion 55 is received within the associated opening 49 of the front section 45 and suitably retained therein, such as by an adhesive. The outer surface of the large-diameter portion 53 has a plurality (three being illustrated) of identical, circumferentially arranged, helical slots 59.

One of the negative lenses 31 is suitably fixedly mounted within the small-diameter portion 55 as by an adhesive. The small-diameter portion 55 may have an internal ledge 61 against which the lens 31 is seated to axially position that lens and an inner peripheral surface 62 for locating the lens 31 radially.

The mounting section 41 also includes a lens retainer 63 which, in this embodiment, is a ring having a groove 65 for receiving one of the positive lenses 29. The lens 29 is axially and radially positioned by the walls of the groove and is suitably fixedly attached to the lens retainer 63 as by an adhesive.

The lens retainer 63 is received within the large-diameter portion 53 and is attached to an external adjusting ring 67 by three screws 69 (only two being shown in FIG. 4.) Each of the screws 69 extends through an associated one of the slots 59.

With this arrangement, the lenses 29 and 31 within each of the mounting sections 41 are held in proper axial alignment. In addition, the axial spacing between the lenses 29 and 31 within each of the mounting sections 41 can be varied without varying the vertex distance between the negative lens 31 and the eye. More specifically, by rotating the adjusting ring 67, the screws 69 are moved along the associated helical slots 59 to rotate the lens retainer 63 and the positive lens 29 and to move them axially toward the negative lens 31. Of course, by counter-rotating the adjusting ring 67, the positive lens 29 can be moved axially away from the negative lens 31. Regardless of the direction of axial movement of the positive lens 29, the negative lens 31 remains stationary so that the vertex distance between it and the eye remains the same. Consequently, any astigmatism correction that is placed on the posterior surface of the lens 31 is not upset by movement of the lens 31. In this manner, the magnification achieved by each of the lens sets can be independently varied by rotation of the adjusting rings 67.

Although an exemplary embodiment of the invention has been shown and described, many changes, modifications and substitutions may be made by one having ordinary skill in the art without necessarily departing from the spirit and scope of this invention.

We claim:

1. An ophthalmic lens system comprising:
   an intraocular lens adapted for implantation in the eye and having a negative intraocular lens portion; and
   spectacles including a telephoto lens system comprising a positive lens and a negative lens, said negative lens being located posteriorly of the positive lens.

2. A system as defined in claim 1 wherein the positive lens and the negative lens are the only refracting elements of the lens system which have a power other than unity.

3. A system as defined in claim 1 wherein the positive lens and the negative lens are axially spaced and the positive lens system includes means for adjusting such axial spacing.

4. A system as defined in claim 1 wherein the spectacles include a spectacle frame and means for mounting the positive and negative lenses on the spectacle frame in axial alignment with each other.

5. A system as defined in claim 4 wherein the positive lens and the negative lens are axially spaced and the positive lens system includes means for adjusting such axial spacing without varying a vertex distance by which the negative lens is spaced from an anterior surface of the eye.

6. An ophthalmic lens system comprising:
   an intraocular lens adapted for implantation in the eye and having a negative intraocular lens portion;
   spectacles including a telephoto lens system adapted to be located outside the eye and including a plurality of lenses each having a power other than unity; and
   said spectacles including a spectacle frame and means for mounting said plurality of lenses on the spectacle frame.

7. A system as defined in claim 6 wherein said plurality of lenses includes axially spaced anterior and posterior lenses and the telephoto lens system includes means for adjusting the axial spacing of the anterior and posterior lenses without varying a vertex distance by which the posterior lens is spaced from an anterior surface of the eye.

8. An ophthalmic lens system comprising:
   an intraocular lens adapted for implantation in the eye;
   spectacles including a first telephoto lens system adapted to be located outside the eye and including a plurality of lenses each having a power other than unity; and
   said intraocular lens being adapted to cooperate with said telephoto lens system of the spectacles to provide a second telephoto lens system.

9. A method for obtaining optical magnification with a reduced vertex distance comprising passing light through an external telephoto lens system which includes multiple lenses carried outside an eye by a spectacle frame and then through a negative intraocular lens portion located within the eye.

10. A method as defined in claim 9 wherein the telephoto lens system includes positive and negative lenses and the step of passing includes passing the light through the positive lens and then through the negative lens.

* * * * *